United States Patent
Tao et al.

(10) Patent No.: US 7,572,999 B2
(45) Date of Patent: Aug. 11, 2009

(54) INDUCTIVELY-COUPLED PLASMA TORCH FOR SIMULTANEOUS INTRODUCTION OF GASEOUS AND LIQUID SAMPLES

(75) Inventors: Hiroaki Tao, Ibaraki (JP); Tetsuya Nakazato, Ibaraki (JP); Kenichi Sakata, Tokyo (JP)

(73) Assignees: National Institute of Advanced Industrial Science and Technology, Tokyo (JP); Agilent Technologies, Inc., Palo Alto, CA (US)

( * ) Notice: Subject to any disclaimer, the term of this patent is extended or adjusted under 35 U.S.C. 154(b) by 390 days.

(21) Appl. No.: 11/184,671

(22) Filed: Jul. 19, 2005

(65) Prior Publication Data

US 2006/0024199 A1    Feb. 2, 2006

(30) Foreign Application Priority Data

Jul. 29, 2004    (JP)    ............................. 2004-221292

(51) Int. Cl.
    *B23K 10/00*    (2006.01)
(52) U.S. Cl. ............................. 219/121.52; 219/121.51; 315/111.51
(58) Field of Classification Search ............ 219/121.48, 219/121.51, 121.52, 121.59, 74, 75; 315/111.51; 118/723 I; 356/316
    See application file for complete search history.

(56) References Cited

U.S. PATENT DOCUMENTS

| | | | | |
|---|---|---|---|---|
| 3,467,471 A | * | 9/1969 | Berry et al. .................... | 356/36 |
| 4,575,609 A | * | 3/1986 | Fassel et al. ........... | 219/121.59 |
| 4,926,021 A | * | 5/1990 | Streusand et al. ...... | 219/121.59 |
| 5,233,156 A | * | 8/1993 | Chan et al. ............. | 219/121.52 |
| 6,166,379 A | * | 12/2000 | Montaser et al. ............ | 250/288 |
| 6,936,787 B2 | * | 8/2005 | Tao et al. ................ | 219/121.51 |
| 2004/0195218 A1 | | 10/2004 | Tao et al. ................ | 219/121.51 |

FOREIGN PATENT DOCUMENTS

JP    2004-158314    3/2004

OTHER PUBLICATIONS

Kim et al. "Construction of a Capillary Gas Chromatography Inductively Coupled Plasma Mass Spectrometry Transfer Line and Application of the Technique to the Analysis of Alkyllead Species in Fuel". Oct. 1992. p. 1147-1149.

Ebdon et al. "Analysis of Geoprophyrins by High-temperature Gas Chromatography Inductively Coupled Plasma Mass Spectrometry and High-performance Liquid Chromatrography Inductively Coupled Plasma Mass Spectrometry." Sep. 1994. p. 939-943.

* cited by examiner

*Primary Examiner*—Mark H Paschall
(74) *Attorney, Agent, or Firm*—Ohlandt, Greeley, Ruggiero & Perle, L.L.P.

(57) ABSTRACT

To provide an inductively-coupled plasma torch capable of realizing a GC analysis or the like and a solution analysis by the same torch without removing a capillary tube, etc. The injector tube of the inductively-coupled plasma torch includes an outer injector tube 11 for introducing an atomized solution sample or the like into the inductively-coupled plasma, and an inner injector tube 12 for introducing gaseous molecules into the inductively-coupled plasma, housed in the outer injector tube as integrated and coaxially with it. The inner injector tube is able to convey make-up gas, and has a capillary tube 4 for conveying gaseous molecules and carrier gas together. For sample introduction in analyzing a gaseous sample, the inner injector tube 12 is used, and for sample introduction in analyzing an aerosol sample, the outer injector tube 11 is used.

7 Claims, 3 Drawing Sheets

(a)

(b)

(a)

(b)

(c)

(a)

(b)

INDUCTIVELY-COUPLED PLASMA TORCH FOR SIMULTANEOUS INTRODUCTION OF GASEOUS AND LIQUID SAMPLES

FIELD OF THE INVENTION

The present invention relates to a torch for introducing a gaseous sample, a solution sample, a dry aerosol sample, or the like into inductively-coupled plasma. In particular, the present invention relates to a torch for introducing gaseous molecules provided from a gas chromatograph (GC) or the like, that is, a gaseous sample to be analyzed, into inductively-coupled plasma (ICP) to analyze by an inductively-coupled plasma optical emission spectrometry (ICP-OES) or an inductively-coupled plasma mass spectrometry (ICP-MS), the torch being capable of effectively introducing all of the gaseous molecules into the center part of the inductively-coupled plasma, and also capable of effectively introducing, without torch replacement, a solution sample atomized by a nebulizer or the like, or a dry aerosol sample produced by laser ablation or the like, into the center part of the inductively-coupled plasma.

PRIOR ARTS

Conventionally, when introducing gaseous molecules provided from a gas chromatograph (GC) or the like into inductively-coupled plasma, it has been difficult to set a sample-introducing tube (capillary tube) on the central axis of the inductively-coupled plasma torch, that is, coaxially with it. For this reason, there has been a problem that gaseous molecules out of the sample-introducing tube are not introduced into the center part of the inductively-coupled plasma, and thereby the sensitivity or accuracy of analysis deteriorates. Such examples include ones. described in A. W. Kim, M. E. Foulkes, L. Ebdon, S. J. Hill, R. L. Patience, A. G. Barwise, S. J. Rowland: J. Anal. At. Spectrom., 7, 11471149 (1992), FIG. 1 and L. Ebdon, E. H. Evans, W. G. Pretorious, S. J. Rowland: J. Anal. At. Spectrom., 9, 939943 (1994), FIG. 1. In contrast to this, in JP-A 2004-158314, a configuration is disclosed that a guide for holding a capillary tube coaxially with the injector tube is provided at the downstream end of the injector tube in the inductively-coupled plasma torch. The inventors have pushed forward tests and studies about the operation and effect of such configuration and have confirmed that the above problem is solved.

However, also in this configuration, while the inductively-coupled plasma torch is used for a GC analysis or the like, a solution sample atomized by a nebulizer or the like can not be introduced into the inductively-coupled plasma. For this reason, when a solution analysis is required, it must be made after removing the capillary tube for conveying gaseous molecules with carrier gas, housed in the injector tube, or also removing the make-up gas tube for conveying make-up gas, after a GC analysis has been finished.

SUMMARY OF THE INVENTION

When the removing is required as described above or conversely when the mounting is carried out, retuning of operation conditions associated with them is required, and much time and manpower are required for this. For this reason, even if the guide proposed in JP-A 2004-158314 is used, it would be resulted that two inductively-coupled plasma mass spectrometers are substantially required for a GC analysis or the like and a solution analysis. It is therefore an object of the present invention to solve such problems by providing an inductively-coupled plasma torch capable of realizing a GC analysis or the like and a solution analysis without removing the capillary tube for conveying gaseous molecules with carrier gas, or the make-up gas tube for conveying make-up gas, housed in the injector tube.

The above problems are solved by making the injector tube of the inductively-coupled plasma torch to be of a duplex structure consisting of an outer injector tube for introducing an atomized solution sample or a dry aerosol sample into inductively-coupled plasma, and an inner injector tube for introducing gaseous molecules with make-up gas into the inductively-coupled plasma. The outer injector tube and the inner injector tube are disposed as integrated and coaxially with each other, and a capillary tube for conveying gaseous molecules with carrier gas extends through the inside of the inner injector tube. Furthermore, the inner injector tube provides a flow path for make-up gas.

The invention provides an inductively-coupled plasma torch for introducing a sample into inductively-coupled plasma through an injector tube, said injector tube comprising:

an inner injector tube, the inside of which a capillary tube for introducing a gaseous sample extends through and which provides a flow path for make-up gas; and an outer injector tube for introducing an atomized solution sample or a dry aerosol sample, disposed outside said inner injector tube integrally and coaxially therewith.

Figure 1:
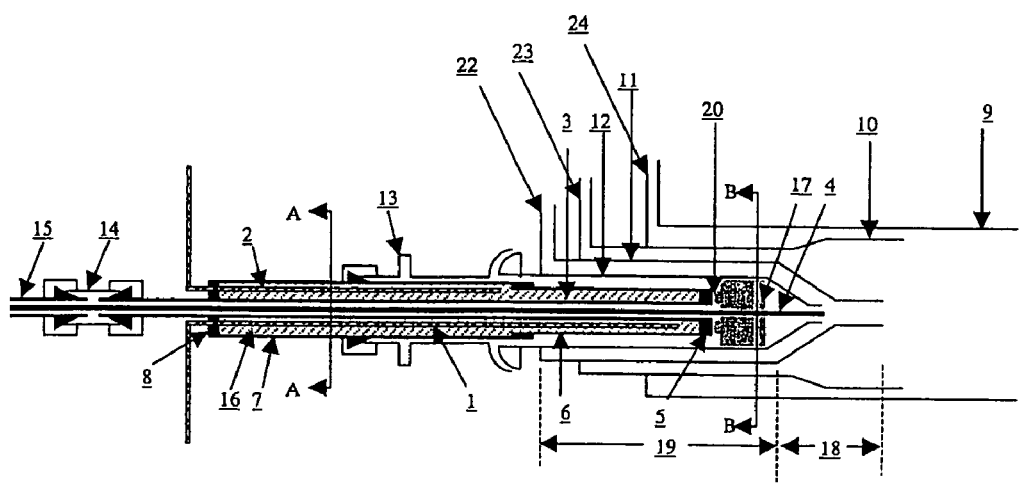
FIG. 1(*a*) is a cross-sectional view of the whole of an inductively-coupled plasma torch along the longitudinal axis according to the present invention, FIG. 1(*b*) is a cross-sectional view taken along line A-A in FIG. 1(*a*), and FIG. 1(*c*) is a cross-sectional view taken along line B-B in FIG. 1(*a*).
Figure 1:
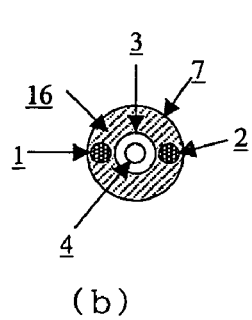
Figure 1:
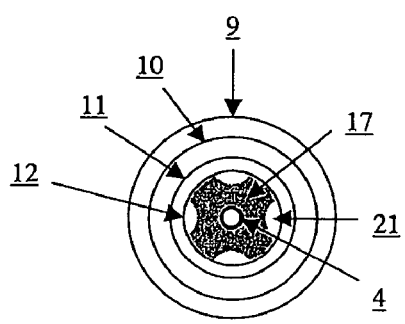

In the drawings, numeral references are:
1: Heater wire
2: Temperature sensor
3: Make-up gas tube
4: Capillary tube
5, 8: Metallic plug
6, 7: Metallic pipe
9: Outermost tube of the inductively-coupled plasma torch
10: Second tube from the outside of the inductively-coupled plasma torch
11: Outer injector tube
12: Inner injector tube
13: Connector with a ball joint
14: Connector
15: Metallic tube extending from a high-temperature source
16: Thermal homogenizing material
17: Guide
18: End portion of the outer injector tube
19: Body of the outer injector tube
20: Protrusion 21: Passage groove
22: Branch tube for nebulizer gas
23: Branch tube for auxiliary gas
24: Branch tube for plasma gas

DETAILED DESCRIPTION OF THE INVENTION

A main feature in configuration of the present invention is that the inductively-coupled plasma torch comprises an outer injector tube for sample introduction, provided outside the inner injector tube integrally therewith. When a gaseous sample is introduced, it is introduced through a capillary tube provided in the inner injector tube. In this case, sample gas and carrier gas introduced from the capillary tube together with make-up gas pass through the small-diameter downstream end portion of the inner injector tube and then the small-diameter downstream end portion of the outer injector tube, and then introduced to the torch downstream end portion where inductively-coupled plasma is generated. On the other hand, when a typical atomized solution sample or a dry aerosol sample produced by laser ablation or the like is introduced, the sample is introduced through the outer injector tube. In this case, an aerosol sample and nebulizer gas sample introduced from the outer injector tube are guided along the outside of the inner injector tube, pass through the small-diameter downstream end portion of the outer injector tube, and are introduced to the torch downstream end portion where inductively-coupled plasma is generated. Thus, the inductively-coupled plasma torch of the present invention has such an advantage that it can be used without replacing parts for respective analyzing of a gaseous sample and an aerosol sample.

The inner injector tube comprises a cylindrical body and a succeeding downstream end portion, and the inner diameter of this downstream end portion is less than that of the body. For example, the downstream end portion may comprise a conical tapered portion having decreasing inner diameter gradually, and a small-inner-diameter portion extending in the axial direction in the form of a cylinder from the vicinity of the top of the conical tapered portion. The capillary tube preferably extends to the downstream end portion of the inner injector tube, despite that it is short. The small-inner-diameter portion has a diameter of at least 1.5 mm or less, and a length of about 2 to 10 mm.

The outer injector tube also comprises a cylindrical body and a succeeding downstream end portion. The outer injector tube has a branch tube at its base portion, and a solution sample atomized by a nebulizer or the like, or a dry aerosol sample produced by laser ablation or the like is introduced from this branch tube to the base portion by nebulizer gas or carrier gas respectively, and is then conveyed to the downstream end portion of the outer injector tube after passing through between the outer injector tube and the inner injector tube. The downstream end portion of the outer injector tube has a cylindrical inner portion having a diameter less than the inner diameter of the body, and the portion between the body and the cylindrical inner portion may be formed so as to be tapered, that is, formed like a cone having an inner diameter decreasing gradually. The inner diameter of the cylindrical inner portion of the outer injector tube downstream end portion is preferably not less than the diameter of the small-inner-diameter portion of the downstream end portion of the inner injector tube. More specifically, the cylindrical inner portion is preferably shaped so as to have at least a diameter of 2.5 mm or less and a length of 3 to 10 mm. Because of this shape, nebulizer gas or carrier gas is introduced to the center part of the inductively-coupled plasma.

The downstream end portion of the inner injector tube is preferably positioned near the cylindrical inner portion. That is, the downstream end portion of the inner injector tube is preferably positioned a few millimeters, preferably about 2 to 5 mm before the cylindrical inner portion, in the axial direction, when viewed from the sample injection side. In this case, the outside of the downstream end portion of the inner injector tube preferably faces the inside of the tapered portion of the downstream end portion of the outer injector tube and has an outline similar to the tapered portion. Furthermore, a capillary tube is disposed so that the downstream end thereof is positioned inside or near the cylindrical inner portion. Usually, this means that the downstream end of the capillary tube is positioned anywhere between a position at a few millimeters, for example, about 3 mm before the cylindrical inner portion in the axial direction (entry side) and a substantially exit position (the downstream end of the outer injector tube), passing over the inside of the cylindrical inner portion.

The inner injector tube includes a guide for holding a capillary tube coaxially with it near its downstream end portion. The guide is shaped like, for example, a cylinder, and has a through hole through which a capillary tube is passed, for holding the capillary tube coaxially with the inner injector tube, and passage grooves or passage holes through which make-up gas passes, having a cross section shaped like a U letter or V letter and extending in the axial direction. Because of this constitution, a capillary tube is coaxially fixed to the inner injector tube, and make-up gas flows smoothly to the end of the inner injector tube. The make-up gas flowing out of the downstream end of the inner injector tube then flows to the downstream end of the outer injector tube and is introduced to the center part of the inductively-coupled plasma. Because of this constitution, the capillary tube is held with stability and coaxially with the inner injector tube. Furthermore, since the inner injector tube is disposed coaxially within the outer injector tube, the capillary tube is held coaxially with the outer injector tube as well.

Make-up gas may be conveyed through the make-up gas tube. In this case, the make-up gas tube is inserted and disposed coaxially within the body of the inner injector tube, and thereby the capillary tube extends coaxially within the make-up gas tube. In this case, the guide may be disposed between the make-up gas tube and the inner injector tube. For example, the guide may be disposed between the downstream end of the make-up gas tube and the downstream end portion of the inner injector tube, being simply held by the inner injector tube, or being fused to the downstream end of the make-up gas tube or the downstream end portion of the inner injector tube.

A thermal homogenizing pipe may be provided coaxially within the inner injector tube in order to keep make-up gas in a high temperature. In this case, a make-up gas tube is provided coaxially within the thermal homogenizing pipe. The thermal homogenizing pipe (heater) may be composed of a heater wire and a temperature sensor, and thermal homogenizing material or filling material as required. As the thermal homogenizing material, ceramic powder, glass beads, metallic wires cut into short pieces, or the like may be used. Alternatively, the thermal homogenizing pipe may consist of a heat pipe. In this case, the heat pipe may be so designed that a make-up gas tube is laid through a through bore provided through the center of the heat pipe, or that the through bore itself is formed as the make-up gas tube. By providing a capillary tube and a make-up gas tube as integrated with a thermal homogenizing pipe in the inner injector tube as stated above, high-boiling point gaseous molecules may be transferred to the inductively-coupled plasma without condensing within a temperature range, e.g., from room temperature to a high-temperature region of 400 degrees centigrade.

Flow paths for make-up gas may be provided also on the axial end face of the guide facing the make-up gas tube, and/or the axial end face of the make-up gas tube or thermal homogenizing pipe facing the guide. For example, the flow paths are formed with protrusions or grooves provided on the axial end face of the guide facing the make-up gas tube, and/or the axial end face of the make-up gas tube or thermal homogenizing pipe facing the guide. Because of this constitution, the make-up gas tube or thermal homogenizing pipe and the guide do not come in intimate contact with each other all over the circumferential direction at the contact portion, and thereby make-up gas may be conveyed smoothly between the make-up gas tube or thermal homogenizing pipe and the guide.

Figure 3:
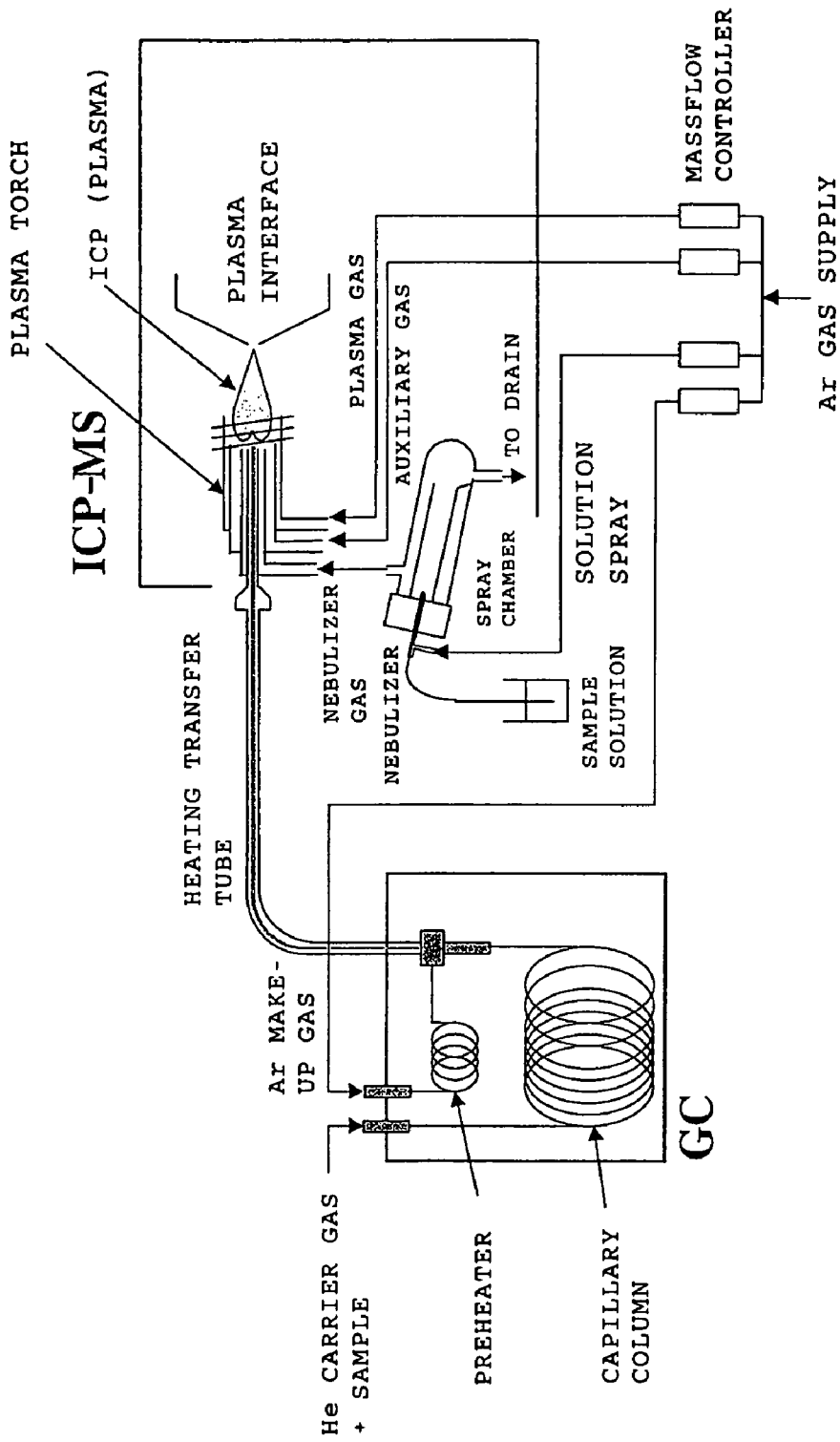
FIG. 3 is a schematic diagram of an inductively-coupled plasma mass spectrometer on which inductively-coupled plasma torch according to the present invention is mounted.

According to the present invention, an inner injector tube installed so as to be able to introduce gaseous molecules provided from a gas chromatograph (GC). or the like into inductively-coupled plasma, and an outer injector tube for introducing an atomized solution sample or the like into the inductively-coupled plasma are disposed coaxially with each other, and thereby it becomes possible to realize a GC analysis or the like and a solution analysis with the same inductively-coupled plasma torch, switching them selectively. Because of this, it becomes possible that optimization of the operation condition of an inductively-coupled plasma mass spectrometer in a GC analysis is carried out with a solution sample, and thereby a gas cylinder for optimization of Xe/Ar gas or the like is not required. Furthermore, as a secondary effect, there is an advantage that an atomized solution sample is heated by the heat conducted from the inner injector tube and is separated into dry aerosol and solvent steam when passing through the outer injector tube, and thereby in an inductively-coupled plasma mass spectrometry, the interference of oxide ions can be decreased, and the sensitivity and accuracy can be increased because of making particle diameters small and uniform. An example of the use of the present invention in an inductively-coupled plasma mass spectrometer is roughly shown in FIG. 3

The present invention is described in more detail below with reference to the accompanied drawings. FIG.1 shows an embodiment of an inductively-coupled plasma torch according to the present invention. FIG. 1(a) is an overview of the inductively-coupled plasma torch, FIG. 1(b) shows a cross section taken along line A-A of FIG. 1(a), and FIG. 1(c) shows a cross section taken along line B-B in FIG. 1(a). In FIG. 1(a), in an outer injector tube 11 for introducing an atomized solution sample or the like into plasma by nebulizer gas, an inner injector tube 12 for introducing gaseous molecules provided from GC or the like into plasma is provided as integrally as well as coaxially with the outer injector tube 11. In the inner injector tube 12, a metallic make-up gas tube 3 for conveying make-up gas such as argon (Ar) gas is provided, and further inside of the tube 3 a capillary tube 4 for introducing gaseous molecules of a sample to be analyzed is provided. In the embodiment shown here, the make-up gas tube 3 and the capillary tube 4 are housed in a thermal homogenizing pipe which is composed of a heater wire 1, a temperature sensor 2, and thermal homogenizing material 16. The pipe itself is made of metallic material. Both ends of this metallic pipe are closed with metallic plugs 5 and 8 and the make-up gas tube 3 and the capillary tube 4 are integrated with the thermal homogenizing pipe. Alternatively, the end faces of the metallic pipe may be closed with silver blazing, heat resistant ceramic adhesive, or the like instead of fitted plugs. The integrated make-up gas tube 3, capillary tube 4, and thermal homogenizing pipe are coaxially inserted in the body of the inner injector tube 12 of an inductively-coupled plasma torch, and are coupled with the inner injector tube using a ball joint 13 having a connector. At the end face of the metallic plug 5, that is, at the downstream end of the make-up gas tube 3, a cylindrical guide 17 is held and disposed so as to be coaxial with the inner injector tube 12.

The downstream end of the capillary tube 4 is positioned near the cylindrical inner portion of the outer injector tube 11, more specifically, a few millimeters before in the axial direction when viewed from the sample injection side. The downstream end may be extended and positioned in the cylindrical inner portion. However, as shown in the figure, the downstream end portion of the inner injector tube is preferably positioned near the cylindrical inner portion or a few millimeters away therefrom, and thereby in many cases the downstream end of the capillary tube extends as far as the downstream end portion of the inner injector tube. In general, the downstream end of the capillary tube is preferably positioned in the range between the downstream end portion of the inner injector tube and the midpoint of the cylindrical inner portion of the outer injector tube. The inner surface of the downstream end portion of the outer injector tube and the outer surface of the downstream end portion of the inner injector tube have preferably similar profile to form a uniform flow path therebetween.

The guide 17 holds the capillary tube 4 in the through hole at the center part thereof such that the capillary tube 4 is placed coaxially with the inner injector tube 12 and the outer injector tube 11. In addition, the guide 17 has passage grooves 21 for conveying make-up gas, penetrating in the axial direction, and protrusions 20 are provided on the end face facing the make-up gas tube 3 so as not to prevent the flow of make-up gas. Because of this constitution, the make-up gas which has flowed through the inside of the make-up gas tube 3 passes through the passage grooves 21 on the circumferential surface of the guide 17, merges at the downstream end portion of the inner injector tube 12 to the carrier gas which has flowed through the inside of the capillary tube 4, or merges at the end portion 18 of the outer injector tube 11 to the nebulizer gas which has flowed through the inside of the outer injector tube 11, which is then smoothly introduced into the center part of the inductively-coupled plasma as a laminar flow. In order to stabilize the laminar flow, the cylindrical inner portion of the downstream end portion of the outer injector tube 11 preferably extends with a uniform diameter for a length of 3 to 10 mm. Furthermore, in this embodiment, the end face of the downstream end portion of the injector tube 12 facing the guide 17 is shaped like a truncated circular cone.

The guide 17 is made of material having high heat resistance and good thermal conductivity, such as quartz glass, metal, ceramic, or the like. Materials for metallic pipes and metallic plugs include stainless steel, while other metal or ceramic may also be used if it is heat resistant and noncorrosive material. As the capillary tube 4, a silica capillary tube or a stainless steel capillary tube is used which is used for a gas chromatograph and the inner surface of which is inactivated, while a tube made of other material may be used as well if the inner surface thereof is inactivated. In this embodiment, the metallic pipe consists of metallic pipes 6 and 7, which are welded to each other to be a single pipe, while one single pipe unnecessary to be welded may also be used.

FIG. 1(b) shows the state that the heater wire 1, temperature sensor 2, and thermal homogenizing material 16 are housed in the metallic pipe 7, and that the make-up gas tube 3 and capillary tube 4 are disposed coaxially with the metallic pipe 7. FIG. 1(c) shows the state that the inner injector tube 12 is installed coaxially with the outer injector tube 11. In addition, FIG. 1(c) shows the state that the outer surface of the guide 17 and the inner surface of the inner injector tube 12 are in intimate contact with each other at portions other than the passage grooves 21, and that the inner surface of the guide 17 and the outer surface of the capillary tube 4 are in intimate contact with each other.

The operation of the inductively-coupled plasma torch arranged as stated above is described below. The heater wire 1 serves to supply heat by electric resistance heating, and the difference between the temperature measured by the temperature sensor 2 and the preset temperature is used for the adjustment of current supplied to the heater wire 1. The metallic pipes 6, 7 house the temperature sensor and the thermal homogenizing material 16 so that the internal temperature therein is kept even. The metallic plugs 5 and 8 are provided on the end portions of the metallic pipe respectively, so that the thermal homogenizing material 16 does not fall off the metallic pipe. The ball joint with a connector 13 connects the metallic pipe to the inner injector tube 12 such that the position of the metallic pipe relative to the inner injector tube is adjustable in order to prevent the external air from entering the inner injector tube 12 of the inductively-coupled plasma torch. High-boiling point gaseous molecules provided from a high-temperature source such as a GC, pyrolyzer, or TG, and carrier gas such as helium (He) gas for carrying the high-boiling point gaseous molecules to the inductively-coupled plasma are introduced through the capillary tube 4 to the inductively-coupled plasma in the right direction in FIG. 1(a). Make-up gas is guided in the right direction in FIG. 1(a) through the inside of the metallic make-up gas tube 3 having the function of protecting the capillary tube 4 against damage, the passage grooves 21 of the guide 17, the inner injector tube 12, and the cylindrical inner portion of the outer injector tube 11. Such an arrangement has an advantage of allowing gas to pass through the center of the outer injector tube as a laminar flow.

Make-up gas is used for flow control of sample gas, carrier gas of GC, nebulizer gas, and total injector gas, and is used as a medium for conducting heat to the sample gas when a thermal homogenizing pipe is provided. As described above, according to the present invention, there is an advantage that a GC analysis or the like and a solution analysis can be made with the same inductively-coupled plasma torch through switching them selectively, and it is also possible to keep nebulizer gas flowing when making only GC analysis or the like excluding a solution analysis. Conversely, when making only solution analysis excluding GC analysis or the like, it is also possible to keep flowing not only make-up gas in the make-up gas tube 3 but also carrier gas of GC.

The guide 17 has a function of holding the capillary tube 4 on the axis of the downstream end portion of the inner injector tube 12 as well as the function of conveying the make-up gas through the passage grooves 21. In this embodiment, the downstream end portion of the inner injector tube 12 has an inner diameter less than that of the body of the inner injector tube 12 to provide a function of increasing the flow velocity of the make-up gas to introduce effectively the make-up gas and carrier gas into the center part of the inductively-coupled plasma, and also a function of fixing the position of the guide 17 so that the guide 17 is not pushed and moved to the right direction in FIG. 1(a) by the make-up gas. And the protrusions 20 prevent the guide 17 from blocking the outlet of the make-up gas tube 3 to interfere with the flow of make-up gas.

A principal distinctive operation according to the arrangement of the present invention relates to the use of the outer injector tube. The branch tube 22 for nebulizer gas provided on the base portion of the outer injector tube 11 is used to introduce nebulizer gas or carrier gas for carrying a solution sample atomized by a nebulizer or the like, or a dry aerosol sample produced by laser ablation or the like. The body portion 19 of the outer injector tube 11 has the function of conducting nebulizer gas or carrier gas to the end portion 18. The downstream end portion 18 of the outer injector tube 11 has a conical portion having an inner diameter decreasing gradually from the body 19, and a cylindrical inner portion provided at its end, the inner diameter of the cylindrical inner portion being less than the inner diameter of the body 19 of the outer injector tube 11. This shape functions so as to introduce effectively nebulizer gas or carrier gas to the center part of the inductively-coupled plasma.

EXAMPLES

Furthermore, the present invention will be described in more detail with a more specific embodiment. As a capillary tube 4 for introducing gaseous molecules, a silica capillary tube used for gas chromatograph is used, and the inner surface thereof is inactivated having an inner diameter of 0.32 mm and an outer diameter of about 0.5 mm. As a make-up gas tube 3, a stainless steel tube having an outer diameter of 1.59 mm and an inner diameter of 1.00 mm is used. One end of the make-up gas tube 3 is connected to the metallic tube 15 extending from a high-temperature source by a connector 14. As a matter of course, this connecting portion is heated and thermally homogenized by a well-known prior method so that high-boiling point compound does not condense. The make-up gas tube 3 is housed together with a heater wire 1 and a temperature sensor 2 in a metallic pipe (formed into a single pipe by welding metallic pipes 6 and 7), and the gap in the metallic pipe is filled with thermal homogenizing material 16 for conducting heat evenly. Metallic plugs 5 and 8 are fitted in the metallic pipe so that the thermal homogenizing material does not fall off the metallic pipe. As the metallic pipes 6 and 7, a stainless steel pipe having an outer diameter of 3.40 mm and an inner diameter of 2.84 mm, and a stainless steel pipe having an outer diameter of 6.35 mm and an inner diameter of 4.75 mm are used respectively.

The metallic pipe 7 is coupled to the inductively-coupled plasma torch by the connector 13. The position of the metallic pipe in the axial direction in the inner injector tube 12 can be adjusted with the screw portion of the connector 13 (the left portion of the connector 13 in FIG. 1(a)). Furthermore, the angle between the metallic pipe and the inner injector tube 12 may be adjusted with the ball joint portion of the connector 13 (the right portion of the connector 13 in FIG. 1(a)) such that the metallic pipe becomes parallel with the inner injector tube 12.

Figure 2:
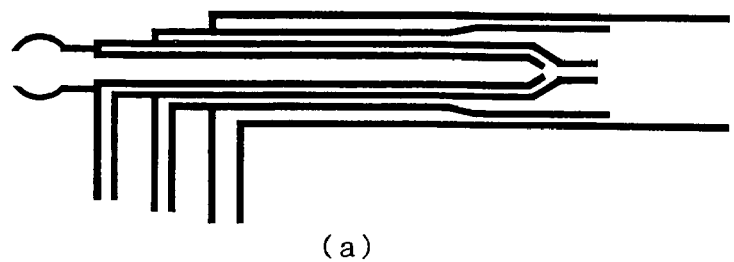
FIG. 2(*a*) is an illustrative view showing an outline of the quadruple-tube structure portion of the inductively-coupled plasma torch according to the present invention, and FIG. 2(*b*) is a cross-sectional view taken along the longitudinal axis, showing the shapes of and the positional relation between the inner injector tube, outer injector tube, and capillary tube according to the present invention.
Figure 2:
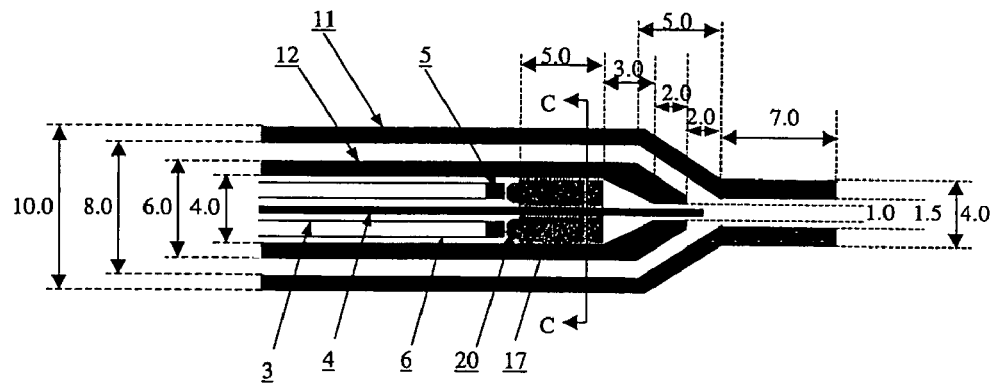

FIG. 2(a) schematically shows the shape of the quadruple-tube structure portion of the inductively-coupled plasma torch according to the present invention. The inner injector tube and outer injector tube according to the present invention form the innermost tube and the second tube from the center of the quadruple-tube, respectively. Functions of the outermost tube and the second tube from the outside are well known by those skilled in the art.

FIG. 2(b) specifically shows the shapes of the inner injector tube 12, outer injector tube 11, and capillary tube 4, and the positional relation between them. As shown in FIG. 2(b), as the guide 17, a quartz glass tube having a through hole with diameter of about 0.5 mm in the center part, an outer diameter of 4.0 mm, and a length of 5.0 mm may be used. The inner diameter of the guide 17 is nearly equal to the outer diameter (about 0.5 mm) of the capillary tube 4, and the outer diameter of the guide 17 is nearly equal to the inner diameter (4.0 mm) of the body portion of the inner injector tube 12.

The downstream end portion of the inner injector tube 12 may be formed, as shown in FIG. 2(b), so that, for example, the inner diameter of the portion having a length of 2.0 mm is 1.0 mm, and the successive portion having a length of 3.0 mm is tapered and shaped like a truncated circular cone having an inner diameter increasing up to 4.0 mm so as to connect to the body. The guide 17 is provided with protrusions 20 on its end face facing the metallic plug 5 in order to ensure flow paths for make-up gas.

In order to install the guide 17, the metallic pipe in which the make-up gas tube 3 is housed, and the capillary tube 4 in the inner injector tube 12, the guide 17 and the metallic pipe are inserted in the inner injector tube 12 in order, and then the capillary tube 4 is inserted in the through hole in the center part of the guide 17. Since the sensitivity obtained by an inductively-coupled plasma mass spectrometry or an inductively-coupled plasma emission spectrometry varies according to the position of the downstream end of the capillary tube 4, the end portions of the inner injector tube 12 and the outer injector tube 11 are preferably made of, e.g., optically transparent material such as quartz glass so that the optimum position of the downstream end of the capillary tube can be adjusted while being monitored. Note that the optimum position of the downstream end of the capillary tube may be adjusted without being monitored. In this case, opaque material may be used for the end portions.

The end portion 18 of the outer injector tube 11 may be formed, as shown in FIG. 2(b), so that, for example, the portion having a length of 7.0 mm of the end portion has a cylindrical inner portion having an inner diameter of 1.5 mm, and the successive portion having a length of 5.0 mm is tapered and shaped like a truncated circular cone having an inner diameter increasing up to 8.0 mm so as to connect to the body portion. The outer diameter of the portion having a length of 7.0 mm of the end portion may be about 4 mm equal to that of an inductively-coupled plasma torch used for an ordinary solution analysis. As a matter of course, other shapes and other dimensions may be applied if the inductively-coupled plasma can be kept with stability.

The invention claimed is:

1. An inductively-coupled plasma torch for introducing a sample into inductively-coupled plasma through an injector tube, said injector tube comprising:
    an inner injector tube, the inside of which (a) has a capillary tube extending therethrough for introducing a gaseous sample, and (b) provides a flow path for make-up gas; and
    an outer injector tube for introducing an atomized solution sample or a dry aerosol sample, disposed outside said inner injector tube integrally and coaxially therewith,
    wherein said inner injector tube comprises a make-up gas tube for said make-up gas, disposed coaxially within said inner injector tube, and said capillary tube is disposed coaxially within said make-up gas tube,
    wherein said inner injector tube comprises a heater for keeping said make-up gas in a high temperature, provided between said inner injector tube and said make-up gas tube,
    wherein said heater comprises a thermal homogenizing pipe having a heater wire and a temperature sensor and/or thermal homogenizing material.

2. The inductively-coupled plasma torch of claim 1, wherein said outer injector tube has a body portion and a downstream end portion, wherein said downstream end portion comprises a cylindrical inner portion having a diameter less than the inner diameter of said body portion, and the downstream end of said capillary tube is positioned inside or near said cylindrical inner portion.

3. The inductively-coupled plasma torch of claim 2, wherein said inner injector tube has a body portion and a downstream end portion having an inner diameter less than the inner diameter of said body portion, and said downstream end portion is positioned near said cylindrical inner portion of said outer injector tube.

4. The inductively-coupled plasma torch of claim 3, wherein the inner diameter of said downstream end portion of said inner injector tube is less than the diameter of said cylindrical inner portion of said outer injector tube.

5. The inductively-coupled plasma torch of claim 1, wherein a guide for holding said capillary tube coaxially with said inner injector tube is provided inside said body portion of said inner injector tube and near said downstream end portion.

6. The inductively-coupled plasma torch of 1, wherein said thermal homogenizing pipe comprises a heat pipe having a through hole at its center, and wherein said make-up gas tube penetrates the through hole of said heat pipe, or the through hole of said heat pipe is formed as said make-up gas tube.

7. The inductively-coupled plasma torch of claim 1, wherein said outer injector tube has an end portion, and wherein said inductively-coupled plasma torch further comprises:
    an outermost tube at said end portion; and
    a second tube within said outermost tube at said end portion, situated coaxially with said outer injector tube and said outermost tube.

* * * * *

UNITED STATES PATENT AND TRADEMARK OFFICE
CERTIFICATE OF CORRECTION

| | |
|---|---|
| PATENT NO. | : 7,572,999 B2 |
| APPLICATION NO. | : 11/184671 |
| DATED | : August 11, 2009 |
| INVENTOR(S) | : Hiroaki Tao et al. |

Page 1 of 1

It is certified that error appears in the above-identified patent and that said Letters Patent is hereby corrected as shown below:

In column 10, line 37, in Claim 6, delete "of 1," and insert -- of claim 1, --, therefor.

Signed and Sealed this

Third Day of November, 2009

David J. Kappos
*Director of the United States Patent and Trademark Office*